United States Patent
Galvez et al.

(10) Patent No.: US 8,316,104 B2
(45) Date of Patent: Nov. 20, 2012

(54) METHOD AND APPARATUS FOR COLLABORATIVE SYSTEM

(75) Inventors: Philippe Galvez, Versonnex (FR); Harvey B. Newman, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 628 days.

(21) Appl. No.: 11/559,881

(22) Filed: Nov. 14, 2006

(65) Prior Publication Data
US 2007/0156813 A1    Jul. 5, 2007

Related U.S. Application Data

(60) Provisional application No. 60/737,045, filed on Nov. 15, 2005.

(51) Int. Cl.
*G06F 15/16* (2006.01)

(52) U.S. Cl. ......... 709/219; 709/204; 709/218; 709/231

(58) Field of Classification Search .......... 709/203–207, 709/223–229, 217–220, 231–232
See application file for complete search history.

(56) References Cited

U.S. PATENT DOCUMENTS

| | | | |
|---|---|---|---|
| 6,459,682 B1 * | 10/2002 | Ellesson et al. | 370/235 |
| 6,484,196 B1 * | 11/2002 | Maurille | 709/206 |
| 6,751,404 B1 * | 6/2004 | Whitford et al. | 386/241 |
| 6,976,066 B1 * | 12/2005 | Mouhanna et al. | 709/223 |
| 7,111,045 B2 * | 9/2006 | Kato et al. | 709/205 |
| 7,266,686 B1 * | 9/2007 | Monteiro et al. | 713/161 |
| 7,346,654 B1 * | 3/2008 | Weiss | 709/204 |
| 2002/0066109 A1 * | 5/2002 | Tam et al. | 725/106 |
| 2002/0133611 A1 * | 9/2002 | Gorsuch et al. | 709/231 |
| 2003/0037109 A1 * | 2/2003 | Newman et al. | 709/204 |
| 2003/0099194 A1 * | 5/2003 | Lee et al. | 370/229 |
| 2004/0193709 A1 * | 9/2004 | Selvaggi et al. | 709/224 |
| 2004/0255323 A1 * | 12/2004 | Varadarajan et al. | 725/25 |
| 2006/0248144 A1 * | 11/2006 | Zhu et al. | 709/205 |

* cited by examiner

*Primary Examiner* — Joshua Joo
(74) *Attorney, Agent, or Firm* — Lyon & Harr, LLP; Richard T. Lyon

(57) ABSTRACT

A collaborative system that includes automatic monitoring and management of reflector/servers and clients. The reflectors are in a logical cluster although their physical locations may be anywhere in the world. Reflector to reflector performance and status is continuously monitored. If a reflector-to-reflector link goes down or is underperforming, the reflector cluster is rerouted to provide desired performance. Clients are monitored and provide information via the network to register/management servers. A best path for the client capabilities is calculated and established. If network performance deteriorates, there are a tiered selection of session modifications that are initiated to compensate. These include reducing video detail levels, reducing number of video streams, reducing size of video windows, adjusting frame rate, and other corrective measures. The client software includes the ability to accept plug-in applications and functionality for customizable operation.

11 Claims, 10 Drawing Sheets

METHOD AND APPARATUS FOR COLLABORATIVE SYSTEM

CROSS-REFERENCE TO RELATED APPLICATIONS

This patent application claims priority to U.S. Provisional Patent Application No. 60/737,043 filed Nov. 15, 2005 and incorporated by reference herein in its entirety.

GOVERNMENT RIGHTS

The U.S. Government has certain rights in this invention pursuant to DOE—Grant No. DE-FG02-92ER40701 T-103069 and National Science Foundation—Grant No. ANI-0230937.

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

BACKGROUND

The "Virtual Rooms Videoconferencing System" (VRVS) is based on the Virtual Rooms concept and is described in U.S. patent application Ser. No. 09/839,847 filed Apr. 20, 2001 entitled Virtual Room Videoconferencing System, assigned to the assignee of the present application and incorporated by reference herein in its entirety. Several participants from different geographical places can have a conference (text, audio, video and shared applications) in a unique virtual area. This space is called a "Virtual Room". VRVS provides a videoconference service over IP networks via an intuitive web-based graphical user interface for non-expert users. VRVS has no frontier and has registered users spread in over 120 countries.

Each member of a virtual conference room makes a connection between their computing device and a reflector. A reflector is a host (server) that interconnects each user to a virtual room. The reflector in turn connects to one or more other reflectors via one or more tunnels (such as a TCP tunnel). A tunnel is a permanent uni-cast or multi-cast connection between reflectors. The reflectors and their links form a set of virtual sub-networks through which audio, video or data, flows. When a user wishes to join a virtual conference, they choose the appropriate room, which in turn causes the system to locate the ideal reflector for that user. The ideal reflector may be the reflector that is closest to the user's system or it may be another reflector that is specifically optimized for that user.

Once the reflector is chosen, all information is passed from the user to all other members of the virtual conference room by sending packets of information from the user, to the reflector, and across one or more tunnels so that the packets are broadcast to each reflector where a member of the virtual conference room is connected and may receive the broadcasted packets. When multiple users are connected to the same reflector, the reflector serves to multiply the stream of packets at the local site, so that each user receives the packet.

SUMMARY

A collaborative system that includes automatic monitoring and management of reflector/servers and clients. The reflectors are in a logical cluster although their physical locations may be anywhere in the world. Reflector to reflector performance and status is continuously monitored. If a reflector-to-reflector link goes down or is underperforming, the reflector cluster is rerouted to provide desired performance. Clients are monitored and provide information via the network to register/management servers. A best path for the client capabilities is calculated and established. If network performance deteriorates, there are a tiered selection of session modifications that are initiated to compensate. These include reducing video detail levels, reducing number of video streams, reducing size of video windows, adjusting frame rate, and other corrective measures. The client software includes the ability to accept plug-in applications and functionality for customizable operation. Having all these monitoring activities between all the different components composing the system (including the end users) provides a global and real-time view/understanding of the entire system which allows the system to take automatic self-correcting/optimized actions in a global scale.

DETAILED DESCRIPTION OF THE PREFERRED EMBODIMENTS

A method and apparatus for providing collaborative system is described. In the following description, numerous details are set forth in order to provide a more thorough understanding of the system. It should be understood that the system may be practiced without these specific details. In other instances, well known features have not been described so as not to obscure the system.

Figure 1:
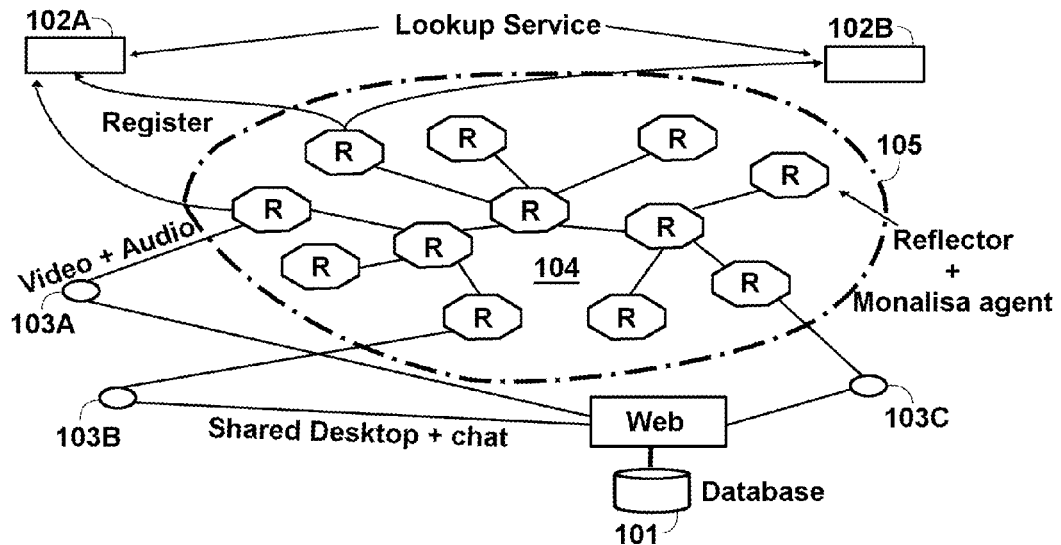
FIG. 1 is a block diagram of an embodiment of a collaborative environment.

A block diagram of an embodiment of a collaborative environment is illustrated in FIG. 1. In descriptions herein, examples may be presented in connection with implementation of a videoconferencing session using the system. It is to be understood that the system is not limited to videoconferencing but applies to a truly collaborative environment where video, audio, text, and other forms of data can be shared simultaneously via the system. Referring to FIG. 1, the collaborative system comprises a database server 101, lookup services 102A and 102B, a number of clients 103A, 103B, and 103C, and a pool 104 of reflectors interconnected via optimized path routing. Dotted line 105 represents the monitored portions of the system.

In this embodiment, each of the reflectors are registered to a high-level directory service so all its peers are automatically and constantly aware of each other's current status and availability. It is seen that this version includes intelligence within the VRVS core network of reflector/servers. This intelligence is implemented using a monitoring environment referred to as MonALISA (Monitoring Agents using a Large Integrated Services Architecture). MonALISA is a globally scalable framework of services to monitor and help manage and optimize the operational performance of Grids, networks and running applications in real-time.

The MonALISA architecture is based on a plurality of layers of global services. The network Lookup Discovery Services (LUS) provides dynamic registration and discovery for all other services and agents. Each MonALISA service can execute many monitoring tasks through the use of a multithreaded execution engine and to host a variety of loosely coupled agents that analyze the collected information in real time. The collected information can be stored locally in databases. The layer of Proxy services provides an intelligent multiplexing of the information requested by the clients or other services and is used for reliable communication between agents. It can also be used as an Access Control Enforcement layer. A service in the MonALISA framework is a component that interacts autonomously with other services either through dynamic proxies or via agents that use self-describing protocols. By using the network of lookup services, a distributed services registry, and the discovery and notification mechanisms, the services are able to access each other seamlessly. The use of dynamic remote event subscription allows a service to register an interest in a selected set of event types, even in the absence of a notification provider at registration time. The lookup discovery service will then automatically notify all the subscribed services, when a new service, or a new service attribute, becomes available.

The code mobility paradigm (mobile agents or dynamic proxies) used in the MonALISA system extends the approaches of remote procedure call and client-server. Both the code and the appropriate parameters are downloaded dynamically into the system. Several advantages of this paradigm are: optimized asynchronous communication and disconnected operation, remote interaction and adaptability, dynamic parallel execution and autonomous mobility. The combination of the service architecture and code mobility makes it possible to build an extensible hierarchy of services that is capable of managing very large systems.

The MonALISA system is give by way of example only. Other monitoring systems may be used without departing from the scope and spirit of the system. The monitoring function should provide the ability to monitor connections, paths, servers, and performance and to react to changes in parameters through re-routing, administrator notification, shut-down, slow-down, or other corrective measures.

Each client 103A-103C is an end user who is participating in a virtual room session using the system. As noted previously, these sessions may be videoconferencing sessions or other collaborative sessions. Although the clients are communicating via the reflector cluster 104, the clients are not in communication with the lookup services 102A and 102B. Thus, there is no active monitoring of the clients during a session.

Figure 2:
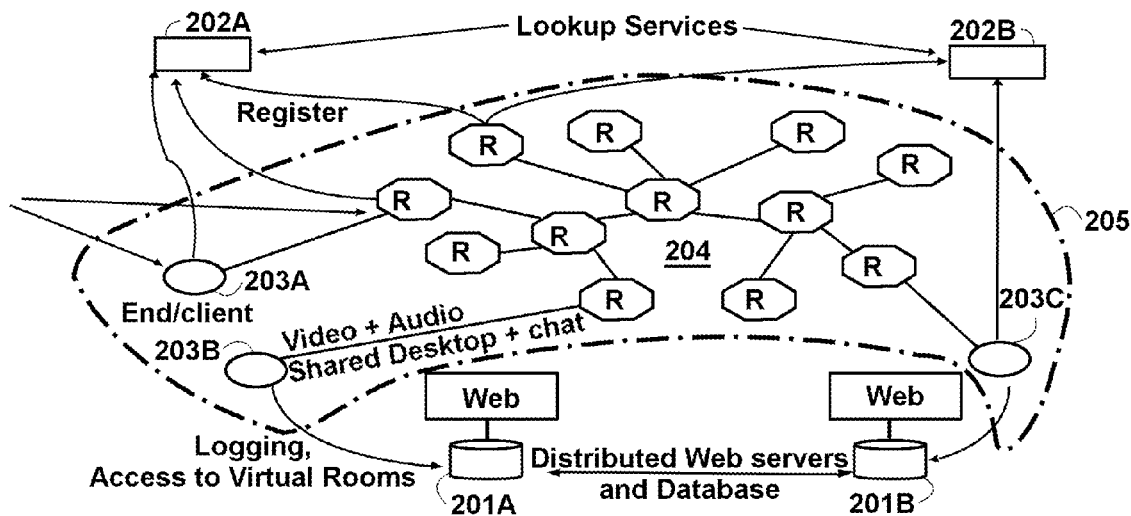
FIG. 2 is a block diagram of an alternate embodiment of a collaborative environment.

FIG. 2 is a block diagram of another embodiment of the system that extends monitoring to the clients. Additional redundancy is provided in the system to reduce or eliminate the chance of single point failure. Referring now to FIG. 2, the collaborative system comprises a pair of database servers 201A and 201B, lookup services 202A and 202B, a number of clients 203A, 203B, and 203C, and a pool 204 of reflectors interconnected via optimized path routing. The dotted line 205 indicating the monitored portion of the system now includes clients 203A, 203B, and 203C.

The system includes a software Client ("client-monitor") that runs on the user's client machine and is part of the software infrastructure, and a Server that is used to provide an intelligent, secure and reliable communication channel between the different entities in the system, and some other services (scheduler, directory services, etc.). Together they provide: support for both reserved and immediate (ad-hoc) point-to-point and multipoint collaborative sessions initiated through Instant Messaging; "adaptive" videoconferencing where the size and numbers of windows are varied automatically if the CPU load on the end-system exceeds a pre-set limit, or if the bandwidth required to sustain the video stream exceeds what is measured to be available; statistics and real-time information (as desired).

When started, the Client-monitor contacts one of several discovery lookup services to ask for the three "nearest" Server reflectors that are currently active and available, selects one of them according to several criteria (location, load, network quality, etc.), and establishes a connection to the best one. First, the client-monitor will try to connect via UDP, the most commonly used protocol for real-time applications, and if that fails (e.g. because some secure networks block UDP), it will use TCP. This mechanism provides a transparent and easy solution for handling many of the firewall and Network Address Translation (NAT) configurations that are often found on campus networks, at home or on travel (DSL, cable or wireless). Once the connection is established, all further communication between the Client-monitor and the system goes through the chosen reflector, using an encrypted data stream.

Figure 8:
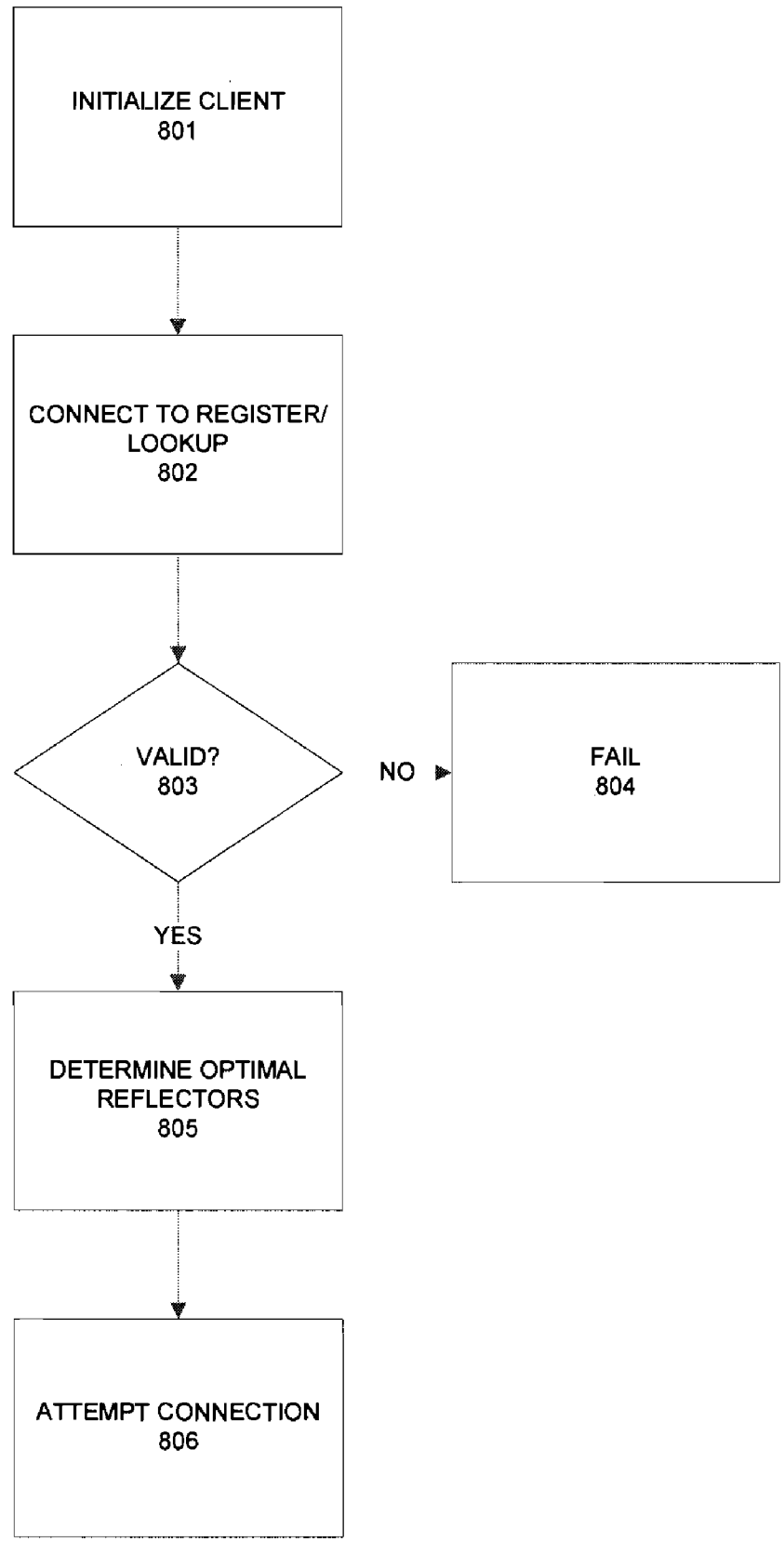
FIG. 8 is a flow diagram illustrating initialization of a client in the system.

This connection process is illustrated in the flow diagram of FIG. 8. At step 801 the client is initialized. At step 802 the client is connected to the register/lookup server. At decision block 803 it is determined if the client is a valid/authorized client. If not, the procedure fails at step 804. If so, the system determines the three optimal reflectors for the client to user for its session at step 805. At step 806 the connection is made following the hierarchy described above trying UDP, then TCP, and the like.

Figure 3:
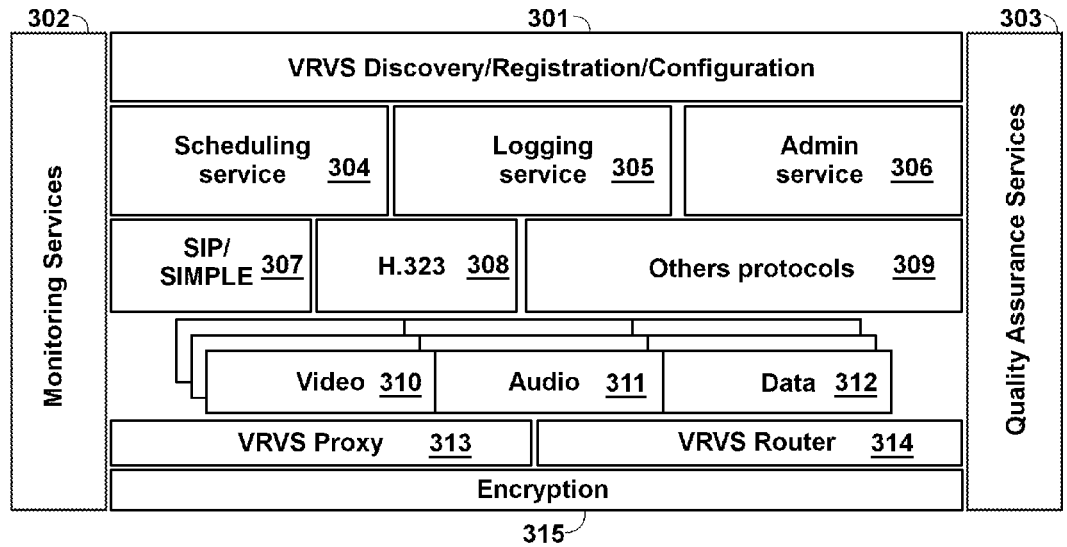
FIG. 3 illustrates the modules in a server of the system.

FIG. 3 illustrates the software modules of the server reflector. When a server reflector (e.g. one of the reflectors from cluster 204) is started, it identifies and registers itself with one of the directory services 202 and obtains its configuration parameters via its Discovery/Registration/Configuration Module 301. The monitoring 302 and quality assurance 303 modules continuously monitor the network quality (packet loss, jitter, latency) between peers and potential peers as well as the system information (CPU, load . . . ). The Quality Assurance module 303 uses this information to take actions (i.e. reroute packets to other peers, restart the software, etc.) and/or send alarms when monitored system or network parameters exceed a preset threshold. The Admin module 306 administers the server reflector by overseeing automatic and secure VRVS code updates, checking on ongoing conferences and the participants' connections to them, adding/deleting/modifying a given connection, etc.). The scheduling 304 and logging 305 modules respectively provide an interface to interact with the database, and allow the user to log into the system and schedule a meeting. Audio/Video/Data threads 310, 311, and 312 are dynamically created for each on-going meeting. These threads manage all the intelligence associated with processing the audio/video/data (including Instant Message) streams. The communication with external entities is via the Proxy module 313 for interacting with clients and via the Router module 314 to communicate with other server reflectors respectively. All communication may be encrypted using encryption module 315. Some additional modules (plug-ins) have been added as needed to support other protocols such as SIP 307, H.323 308 or to remotely control some applications (e.g. sending audio and/or video, mute button) via other protocols 309.

Figure 4:
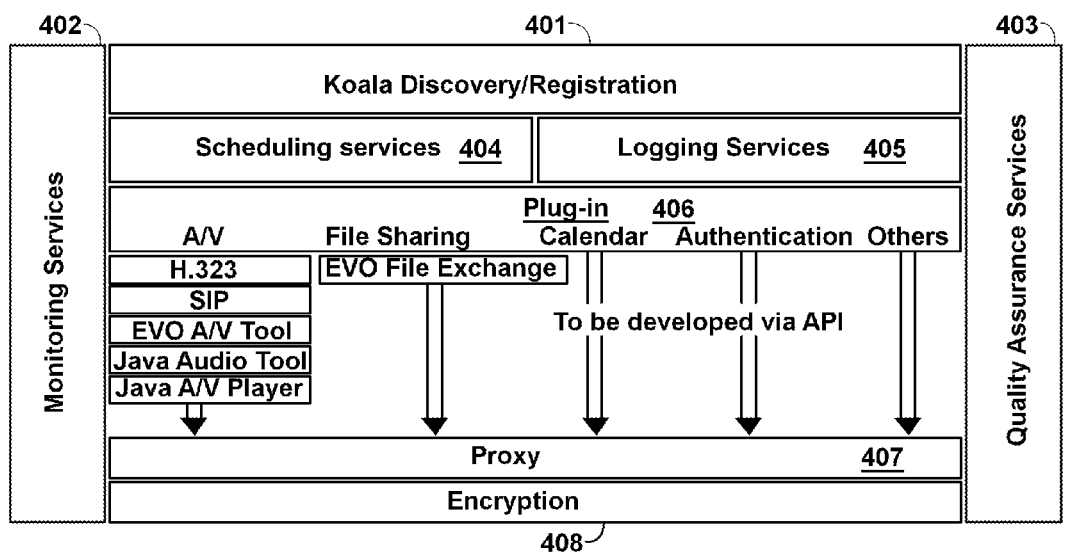
FIG. 4 illustrates the modules in a client of the system.

The Client-monitor architecture is described in FIG. 4. It includes a discovery and registration module 401. When started, the Client-monitor client contacts one of several discovery lookup services to ask for the three "nearest" server reflectors that are currently active and available, selects one of them according to several criteria (location, load, network quality, etc.), and establishes a connection to one. Once the connection is established, all further communication between the Client-monitor client and the system goes through the chosen server reflector, using an encrypted data stream on a single port.

The Client-monitor integrates a client specific MonALISA monitoring module (called LISA) 402 that allows a complete monitoring of the local hardware and system parameters in real-time. This module 402 provides the monitoring service of the Client-monitor client. Being aware in real-time of all the system and network characteristics, we developed a Quality Assurance module 403 within Client-monitor that will send an alarm and/or takes proactive actions in order to provide to the end-user the best quality possible. For example, if the CPU load is too high, Client-monitor will automatically decide to reduce the number of video streams decoded and displayed in the user's computer screen.

A scheduling service component 404 allows a user to create a collaborative session. It may be done by simply booking a meeting or inviting a user to a private meeting via the Instant messaging facility. The logging service module 405 provides an interface for the user to be able to log into the system.

All the communications from the Client-monitor component to the rest of the infrastructure are performed via the proxy module 407. It creates a communication channel using only one port (UDP or TCP) and encapsulates all the traffic (video, audio, IM, presence, logging, booking, etc.). Therefore, it provides an efficient way also to traverse firewall and NAT environments. The Encryption module 408 allows the user to encrypt on the fly any media (video, audio, IM . . . ) he/she wants to receive/send to the collaboration infrastructure.

Because the system is built to be used as a general platform for large collaboration and adapted to many environment and situation, we designed an open architecture offering the possibility to use external components developed by others. The plug-ins 406 concept allows these external components to be added and be selectable by the users to better serve their needs.

The LISA Agent provides:

Complete monitoring of the end-system (load, CPU usage, memory allocation, disk usage, disk 10, paging, running processes, network traffic and connectivity).

Detection of hardware devices on the system and the drivers used by the kernel to control them.

Measurements of end-to-end network performance using different applications (IPERF, WEB100, Ping), which are reported to the user.

A user friendly GUI to present all the measured values and the system parameters.

Filters to trigger actions when predefined conditions are detected.

LISA is integrated in the client-monitor and discovers the running servers (i.e., the reflectors) that are possible candidates to be used by the client. This is done by detecting network proximity (server/reflectors in the same network, region or country) as well as the load on each of the candidate servers and the current number of clients each one is serving. The client-monitor creates a short list of candidate "best" reflectors, taking the load on each reflector as well as the network connectivity to it into account.

End-to-end network performance measurements are performed periodically with the reflectors on the short list, and based on these measurements the LISA agent provides the best candidate to the application program. These measurements are continuously performed in the background and in case the connectivity with the "best service" changes, it will notify the application to reconnect to the new "best service".

Server/Reflector Monitoring

For each server/reflector, a MonALISA service stores the results it monitors locally in an embedded database, in a mode that aims to minimize the server resources it uses (typically less than 16 MB of memory and low system load). Dedicated modules have been developed to interact with the server to (1) collect information about the topology of the server network, (2) monitor and track the traffic among the server/reflectors and report communication errors with the peers, and (3) track the number of clients and active virtual rooms. In addition, overall system information is monitored and reported in real time for each reflector (e.g. load, CPU usage, and total traffic in and out).

The monitoring system provides real-time information about the number of conferences and clients, the topological connectivity of the servers, the quality of the network connectivity along each path in the server/reflector network, along with information on the state of the servers in the network (I/O traffic, CPU load). Clients can also obtain historical data for any of these parameters.

Maintaining and controlling large-scale distributed systems can be a very time consuming job. For this reason, in addition to dedicated monitoring modules and filters for the system, agents are utilized that are able to supervise the running of the system servers automatically.

If a server/reflector software stops (or does not answer monitoring requests correctly) the agent will try to restart it automatically. This is done for the entire server/reflector or only for specific components. If this operation fails twice, the agent will send a notification email or SMS message to a list of administrators. Such agents are the first generation of a family of modules that are capable of reacting to, and taking well-defined actions following errors in the system. MonALISA also provides an administrative graphical user interface which connects to any reflector using SSL with X.509 certificates. Each MonALISA service keeps a list of trusted administrator certificates in a private keystore. An authenticated administrator is allowed to update the server/reflector software, stop/restart the software, and load agents with new monitoring modules.

The system uses a global service which subscribes to connectivity information from all the server/reflectors and analyzes it 24×7 in real-time. It has several levels of alarm-triggers and informs the relevant administrator(s) by email when a problem is detected such as lost connectivity, too high CPU usage, etc. . . .

Figure 5:
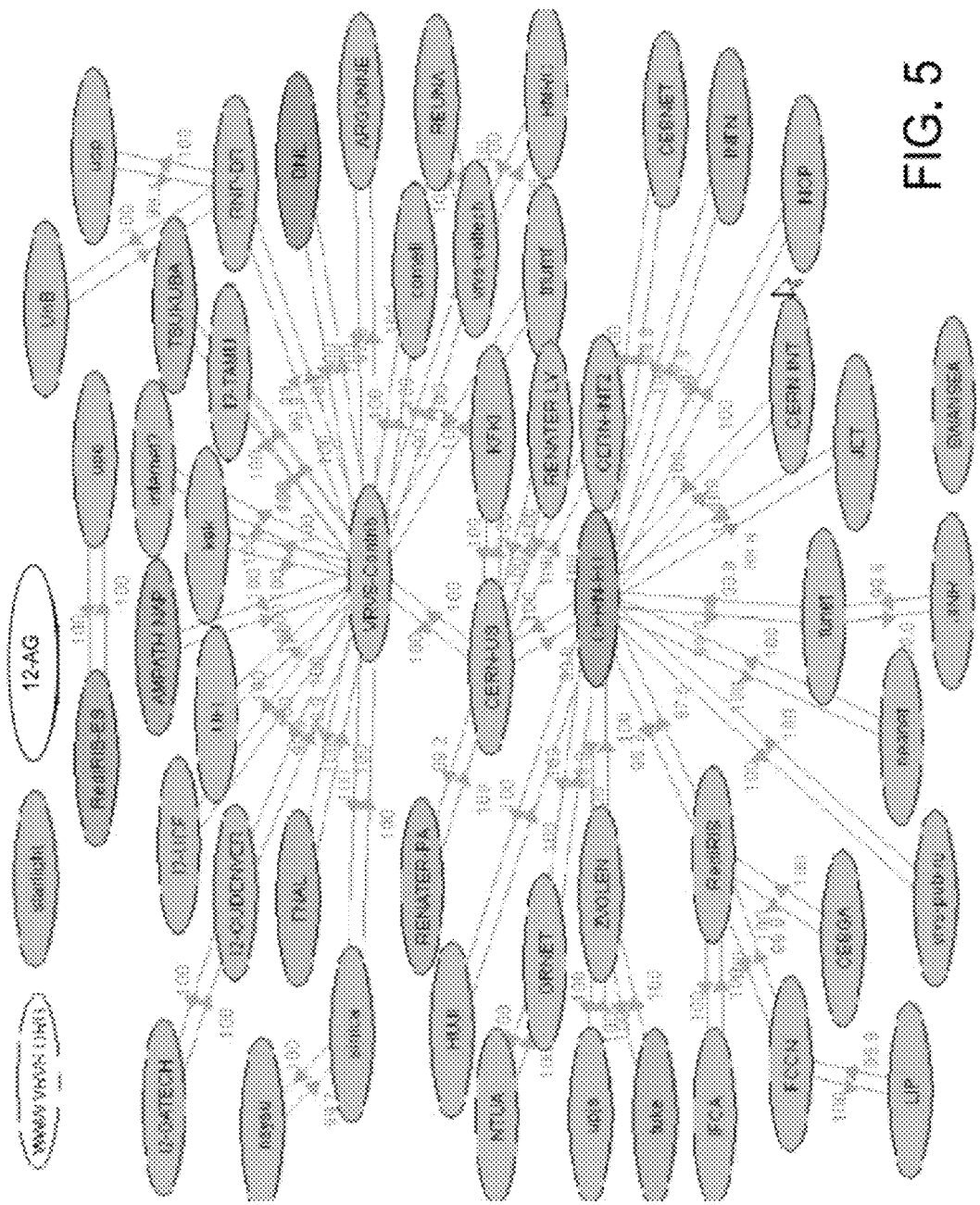
FIG. 5 is a graph illustrating the complexity of the set of interconnections managed by the system.

With the help of MonALISA, the system maintains a connectivity tree that links the server/reflectors. This tree is used to compute the optimal routes for the real-time data streams dynamically, based on information about the quality of alternative possible connections between each pair of server/reflector nodes. If one or more links goes down or is substantially degraded, the tree is rebuilt and re-optimized in real-time, making the system resistant to failures. A typical graph (a snapshot of a picture that evolves with time) illustrating the complexity of the set of interconnections managed by MonALISA is shown in FIG. 5.

Figure 6:
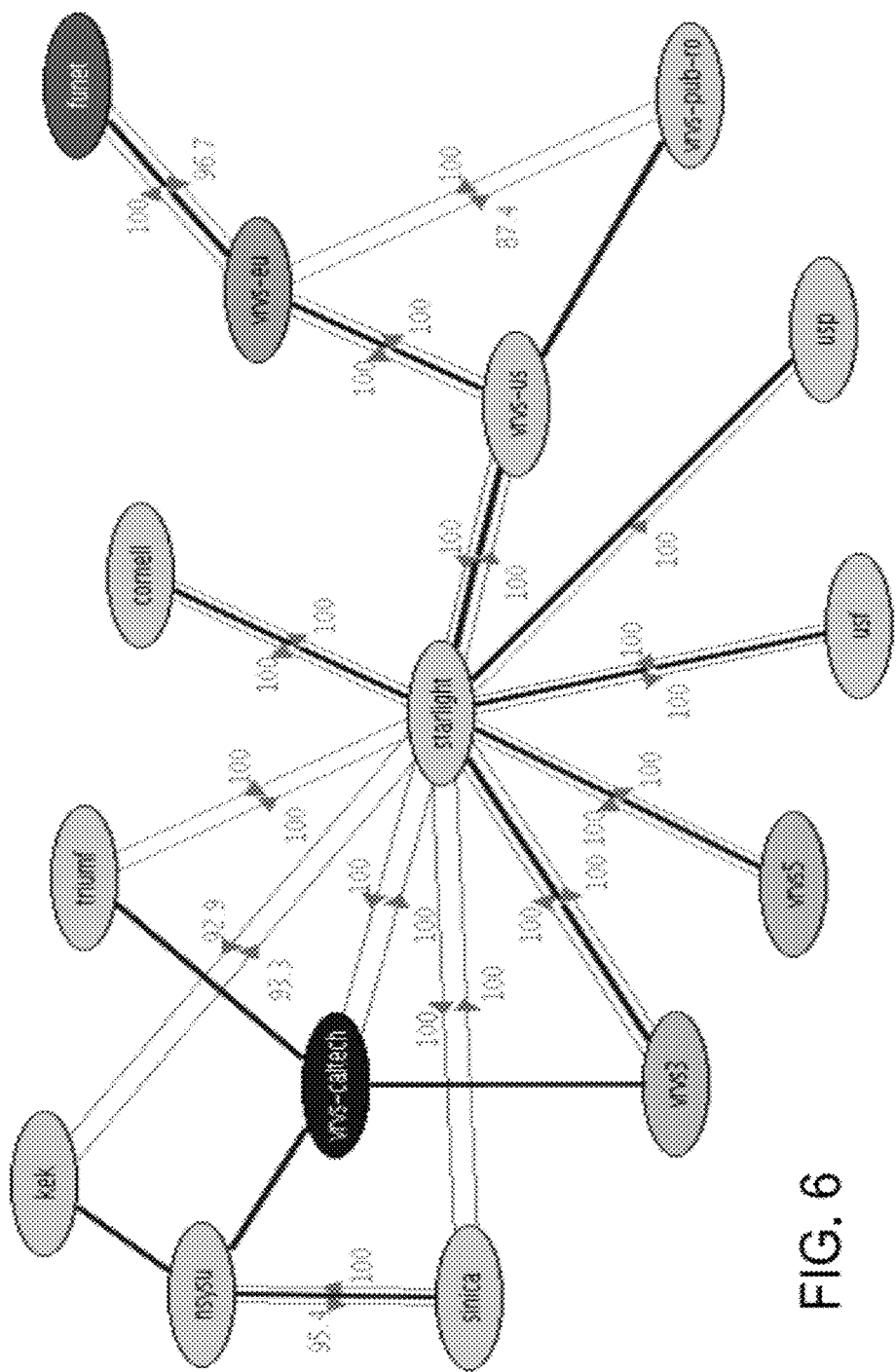
FIG. 6 is a graph illustrating potential peer connections.

In order to find the set of interconnections that optimizes the global data flow, the reflectors and all of the potential peer connections are represented as a graph (FIG. 6). The problem is then to find the "minimal spanning tree" (MST) that links all of the server/reflector nodes (represented by vertices in the graph) for which the total connection "cost" is minimized. The system uses monitoring agents to provide the information needed to compute the MST. These agents are deployed in all MonALISA services, and run continuously (typically every two seconds) making measurements with a selected set of potential peers, using small UDP packets to evaluate the Round Trip Time (RTT), its jitter and the percentage of lost packets. The "cost" of each connection between two server/reflector nodes is then evaluated in real-time using the UDP measurements taken from both sides. If lost packets are detected or if the jitter is high on a link, the cost value for that connection in the tree increases rapidly.

Based on the values provided by the deployed agents, the MST is calculated in near real-time. The MST solution is obtained using an implementation of Boruvka's Algorithm, which is well suited for parallel/distributed processing. However, any suitable means for calculating MST may be used in connection with the system. Once a link is part of the MST a "momentum" factor is attached to that link, which prevents the assigned cost from varying too rapidly. This is to avoid triggering too many reconnections in the tree in response to small fluctuations in the set of measurements. Such cases may occur when two possible peers have very similar parameters (or they may be at the same location). FIG. 6 also shows an example of an MST for connecting the VRVS reflectors, represented by the heavy lines in the figure.

Figure 9:
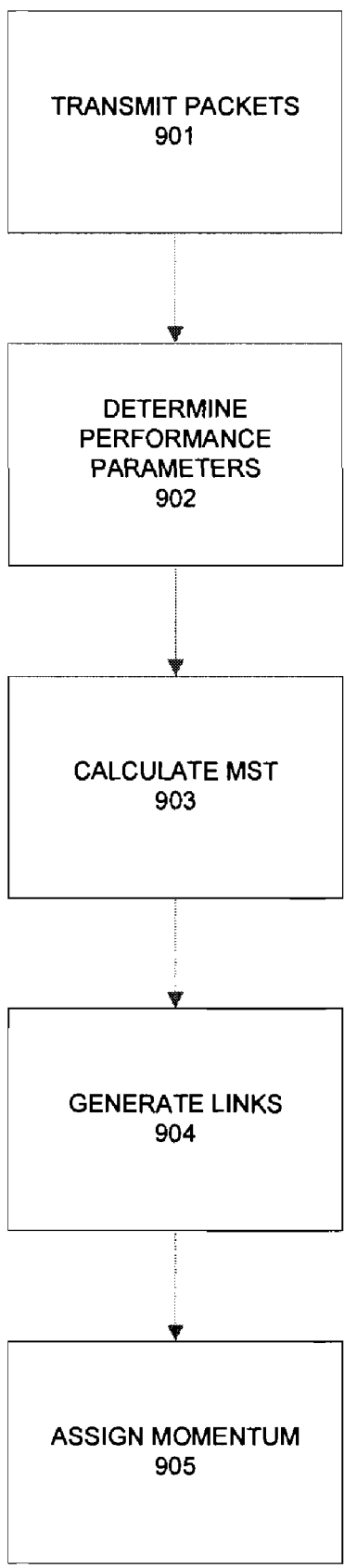
FIG. 9 is a flow diagram illustrating monitoring and management of a reflector in the system.

FIG. 9 is a flow diagram illustrating the monitoring and management of the reflectors and the generation of an MST. At step 901 packets are transmitted between some or all links of the reflector cluster. These packets may be UDP packets or any other packets as desired. At step 902 performance parameters are determined based on the receipt and ACK of these packets. Such performance parameters may include, but are not limited to, RTT, jitter, packet loss, collisions, and the like. At step 903 the performance parameters are used to calculate and MST. At step 904 the links are created for the optimal MST. At step 905 a momentum value is assigned to the links as noted above so that bursty or transient effects do not result in excessive rerouting.

In one embodiment, a generic framework for building "pseudo-clients" for the MonALISA services was developed. This has been used for creating dedicated Web service repositories with selected information from specific groups of MonALISA services. The pseudo-clients use the same set of lookup services to find all the active MonALISA services in a specified set of groups. They subscribe to these services according to a list of predicates and filters that specify the information the pseudo-client wants to collect. The pseudo-client stores all the values it receives from the running services in a local MySQL database. It uses procedures written as Java threads to compress old data.

Logging In

In order to log into the collaborative infrastructure, a user/client needs to be registered into the system. A registration web page is provided where basic information such as first and last name, logging preferred name, password and email are requested. An email is then sent back to the user for confirmation. Currently, the log-in authentication mechanism is provided internally by the EVO infrastructure, but using the plug-in section, interfacing with other authentication mechanisms used by other services or institutions is possible Booking a Meeting The system provides the user four ways to organize a collaborative session in one embodiment of the system.

Permanent Virtual Room: This virtual room is permanently available and so can be accessed at any time. Access can also be protected via a password.

Booking Virtual Room: This virtual room is booked via an advanced calendar interface for a limited time at a specific date. The interface allows a user to book different type of recurrent meetings (daily, weekly, etc.). When, the date/time of the meeting arrives, the virtual room appears in the interface and the users are ready to access it. The virtual room disappears at the end of the booking time. Some basic information is requested during the booking such as the meeting title, the meeting description, start/end date/time and optionally a password.

Ad-Hoc Virtual Room: This virtual room is created on the fly. When a user wants to have a meeting without having to do a booking, the user can simply start an Ad-Hoc virtual room by providing some information such as meeting title, meeting description and optionally a password. When clicking "ok", the meeting is created and the user enters automatically to the virtual room (using his A/V preferred tools) and he/she is ready to collaborate. Instantly, the virtual room information is broadcast to all the others clients so any remote users can join the meeting as well. The default duration for an ad-hoc meeting is 8 hours and will be removed from the list of meetings when no more participants are in the meeting for more than 30 minutes.

Private Meeting: Each user has the possibility to invite remote peer users to a private meeting. The user can optionally add a commentary text in his information message to be received by the remote selected user via a pop-up window (and a ring tone). The invitation could be accepted or declined. In the first case, when the remote user accepts, both the invitee and the user that initiate the invitation are joined instantly in a private virtual room to communicate each other using their preferred tools. At this stage, they can invite other colleagues as well growing from 2 to an indefinite number. In this particular case, the virtual room information is not propagated to the infrastructure so no one except the invited users of the private meeting are aware of the existence of this particular meeting and were/are able to join. (In one embodiment, an invitation can only be sent to a remote user not already in a meeting.)

In one embodiment, for the first three cases mentioned above, when a virtual room is set-up a message is sent to the requester acknowledging that the booking has been successfully done as well as URL information for quick access to the meeting. The URL could be provided to remote potential attendees via email or other means. When the user clicks on the link, two possible scenarios will occur. (1) If they are already logged in, they will automatically join the associated meeting referenced by the URL. (2) If they are not logged in, then the client will start, the login prompt will appear and if the user enters correctly his/her username and password, he will automatically join the meeting referenced by the URL.

Meeting Management in a Virtual Room

As described above, the user will join a virtual room either by clicking on a permanent, booked or ad-hoc meeting which appears on the list of on-going meeting or invited/be invited to a private meeting. There are a number of activities and functions supported that may be accessed or used during a meeting.

One can initiate a personal chat with any of the attendees. Being a moderator provides the right to do the following on any of the meeting attendees: Mute/Unmute audio, Mute/Unmute video, kick the user out of the meeting, or add the user as a moderator.

One window provides advanced control and setup interface for the Audio/Video plug-in/tool selected by the user to enter to the meeting. They are part of the A/V plug-in and attached to the A/V tools used.

The system permits the sharing of documents between the attendees in this virtual sharing space. The users are capable of uploading and downloading any files of any type and any size in this dedicated shared files space or sending this file directly to any particular attendee. The user has also the possibility to access all the files he/she downloaded locally via the system infrastructure.

Instant Messaging, Presence Information and Chat

The current IM functionality is organized in a tree structure as follows. Several communities are defined from which the user has to select when first registered to the system. Each community includes a "Users" sub-tree structure containing all the logged users belonging to the community and a "Meetings". The IM tree is built dynamically in function of the ongoing meetings and logged users. The user can collapse or expand any parts of the tree structure for better view and accessibility.

In one embodiment, when in a meeting, the current attendees icons which appears in the middle frame of the ongoing meeting tab and specific icon are displayed in the IM user sub-tree of the GUI to indicate that the users are in a meeting. One can position the mouse in the user icon to show detailed information about this user including the meeting he is attending.

There are indicators of presence information so the local user can inform his/her peers colleagues about his status. Currently, the following presence information is provided: "Available", "Away", "Do not disturb, "Out to lunch" and "_Custom" (Allowing the user to specify a custom message status that will be broadcast to all participants on his community, i.e. "Will be back in my office at noon".

Chat window communication is organized in tabs windows. By default the chat tab windows associated with the community is available so all logged users from the same community can exchange messages. When entering a meeting, a new chat tab window associated with this meeting is created (and removed when leaving the meeting). This newly created chat window allows chat communication between attendees of the same meeting. When the user initiates a private chat with any of his/her peers then a private tab chat window is created. This new tab chat window is created for each private chat the user wish to start with any of his peers. The user has the freedom to switch between all the chat tab windows to communicate with his/her community peers, the meeting attendees' peers and his/her private chat channel opened with particular peers.

Firewall and NAT Transversal

The system architecture provides a way to accommodate and cross most firewall and NAT environments. First, all the communication between the client and the reflectors (servers building the overlay network infrastructure) are done only via a single unique port in one embodiment. It means that all the communication processes performed by the client (logging process, booking process, joining process, chat, IM, Presence information, video stream, audio stream, etc.) are using a single port for communication to a unique dedicated reflector server. The use of a single port simplifies considerably the communication set-up from a user and site administrator perspective.

In addition, the client and reflector are capable of having dynamic port source mapping which allows communications to cross most of the NAT environments (so far, we are not aware of a NAT environment that prevents the client from interacting with the reflector server).

By default in one embodiment, the communication is done using the connectionless protocol UDP which is the most efficient for real-time communication. But there are some situations where strong firewall rules prevent any communication via the UDP protocol. In such case, the client is capable of detecting this firewall restriction and will use instead the TCP protocol for communicating with its corresponding reflector/server. Some sites do not block TCP connection initiated from the inside. With this architecture and capability, most users should be able to connect and use the system infrastructure without any problems transparently from their local firewall and NAT set-up.

Security and Encryption

The system architecture includes different level of security. One is on the ability to secure the deployment and access of the collaboration infrastructure. The second level is on the collaboration session itself and the ability to secure the access to a session and/or encrypt the data communication channel.

Securing the EVO Infrastructure

The servers installed in the infrastructure and used to create this efficient overlay network need to run certain system components. One component is the reflector software that handles all the real-time communications and interaction with the clients. In order to be started, the IP address of the server needs to be entered in the system database and enabled. Then, once the reflector software starts, it will connected the system database via a secure RMI connection and if its IP address is matching the one on the database, it will be able to start; otherwise it will simply stop. The second component is the MonALISA software which allows the fully monitoring of the server and its peers and performs self-adjustments such as rebuilding the overlay reflector topology among other things. Without the MonALISA service running on the server (or some other authorized monitoring system) the reflector node will never be integrated in the running reflector topology and so no connection will be possible from the client since it will never be seen and so selected. To start the MonALISA software, we need to provide a signed certificate associated with the local IP address of the server in the configuration set-up directory. When the MonALISA software starts, it will discover and register to a look up directory service. Its local IP address as well as its signed certificate will be checked to assure that it is authorized to register to this directory service. It the case of failure to register, the MonALISA software will stop and the reflector node will never be seen as an active node in the system infrastructure.

Figure 7:
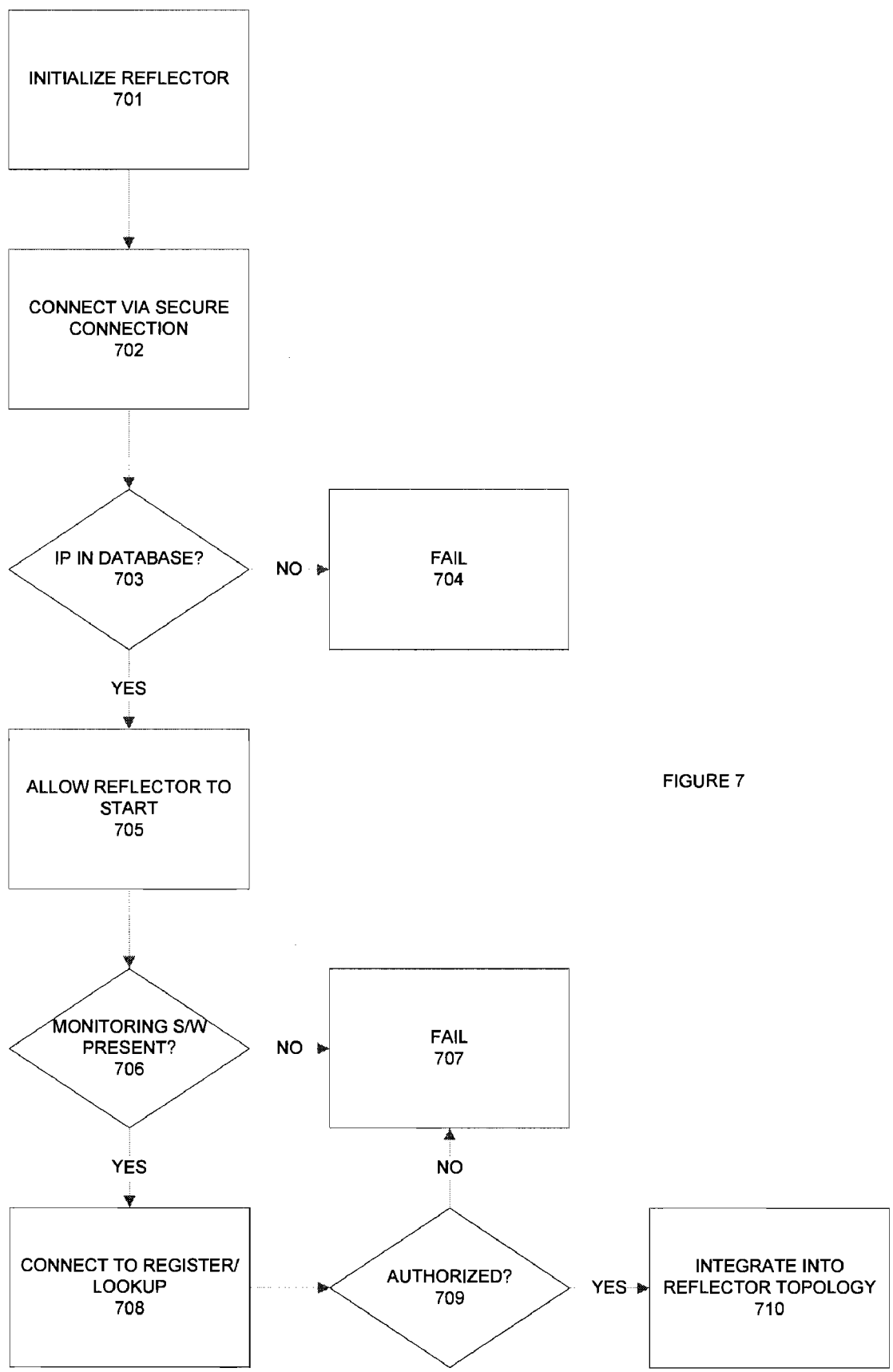
FIG. 7 is a flow diagram illustrating initialization of a reflector in the system.

This operation is illustrated in the flow diagram of FIG. 7. At step 701 the reflector is initialized. At step 702 a secure (e.g. RMI) connection is made with system database. At decision block 703 it is determined if the IP of the reflector matches a value in the database. If not, the initialization fails at step 704. If so, the reflector starts at step 705. At decision block 706 it is determined if monitoring software is present (e.g. MonALISA). If not, the operation fails at step 707. If so, the system is connected to the register/lookup server at step 708. At decision block 709 it is determined if the monitoring software is authorized (e.g. by checking for local IP address and signed certificate). If not, the system fails at step 707. If so, the reflector is integrated into the reflector/server topology at step 710. This procedure may also be implemented on re-start of a member reflector of the topology as desired.

Securing the Collaborative Session

When a user creates a meeting session (permanent, booked or ad-hoc virtual rooms), he/she has the possibility to add a password to protect the access to the meeting. So when a collaborator wants to join this particular secure meeting, a pop-pup window appears asking for a password. Without the requested password, the collaborator will not be able to join the meeting. This particular procedure prevents un-invited people from attending meetings (and starting to listen and/or watch the content or even worse, to disturb the session). Nevertheless, it doesn't protect some unfriendly people to sniff and store the IP packets that cross their network and get confidential information by reading or playing back the packet streams. To be protected for this particular case, encryption is needed.

The system provides several levels of Encryption (1) between the client and the reflector server, (2) between the reflector servers themselves The user has the freedom to select on the fly which part of the traffic will be encrypted from his client to/from his attached reflector. The user can select to encrypt the IM/Chat channel and/or the Audio and/or the Video stream. To perform the encryption, one embodiment uses the JCE (Java Cryptography Extension) package and therefore we can use any of the JCE supported encryption algorithms.

The system provides an easy interface to subscribe or unsubscribe to a community. By a simple click a community management window appear and the user can search any community defined in the system and subscribe to it. When subscribing to a new community, a community chat tab windows and a booked meeting tab windows associated with the community will appear (or disappear is unsubscribed).

Via an advanced search engine, the user has the possibility to search for any past/ongoing/future booked meetings following several criteria such as time, specific keywords, per community, etc. . . . He has also the possibility to use for any users registered in the system via keywords and when found to add it in his buddy list, invite him to a meeting and/or start a chat session.

Plug-in Concept

The system architecture has been designed to allow external components to be built and be used over the very efficient distributed infrastructure provide by the system. Via the client interface/plug-in, we provide a door to this efficient real-time infrastructure. The plug-in functionality can address different categories and needs. In one embodiment, the following plug-in categories are supported:

Audio/Video Plug-in:

These tools are aimed to replace the so-called "Mbone" tools. The plug-in allows control of some parameters for the system video/audio applications which are downloaded and updated automatically when using the plug-in.

EVO H.323 plug-in which allows the connection of any H.323 standard devices running in the desktop or an external hardware client (i.e. Polycom Viewstation) or an H.323 MCU. The plug-in allows the H.323 connection configuration with basic parameters such as IP address, E.164 or Alias name and Gatekeeper. The video frame rate and the bandwidth connection could be set as well. It enables different configuration to be saved depending of the environment for quick set-up.

EVO ViEVOJRAT plug-in, ViEVO is an advanced video tool capable of sending and receiving multiple streams at any frame rate and bandwidth and with the possibility to display the video streams received using OpenGL technology and so providing the possibility to have optimized performance and 3D effect. JRAT is a Java Audio Tool that runs on any Java compliant system. Because it is Java-based, it runs smoothly with most systems and thus provides a basic and efficient audio functionality in all circumstances and environment.

EVO Video Player plug-in which provides a video/audio player using the Java Media Framework (JMF) capable to play-back any movies or still image files of any types (i.e. mpeg, mp3, avi, jpeg, etc. . . . ) supported by JMF and transcoded the into H.263/G.711 streams to be sent to the collaborative session and be viewed by all the remote clients.

EVO SIP plug-in (currently in development) will provide a way to connect any SIP compatible client to the system leveraging the optimize EVO infrastructure for the real-time communication.

File Sharing Plug-in:

EVO File Exchange plug-in allows users to Upload/Download files of any format in the collaborative environment/space. Users are also able to exchange files between themselves in a peer-to-peer manner.

Other categories of Plug-ins permit interfacing with the system infrastructure. For example:

Directory Plug-ins: The system will be able to interface and use others Directory mechanisms provided by others services or institutions such as LDAP or interface with the H.350 protocol [12]

Authentication Plug-ins: The system will be able to interface and use others authentication mechanisms provided by others services or institutions Calendar Plug-ins: The system will be able to interface with other calendaring and booking/scheduling mechanisms already in place and running in some institutions or projects Application Sharing and Whiteboard Plug-ins: The system will be able to interface with others Application Sharing and/or white board tools already developed or in development.

Multi-Language Support

The system architecture provides support for several languages. This functionality is useful when the collaborative service offered is worldwide and addresses a large user based. This feature is implemented in system is the following manner in one embodiment. A flat resource file contains all the English terms to translate in the other corresponding language. A match-to-match keyword line are written from English to the new language (English word=Foreign word). The new resource file is then loaded dynamically when the user selects the language he/she wants to use via the client GUI. This selection can be done at any time. When done, all the keywords mentioned in the resource file are translated into the new language in the client GUI. To support a new language, one has just to create this resource file associated with the new desired language.

Local Monitoring Function

A monitoring panel is available from the client interface. When selected, the user is able to monitor in real-time the following information:

Real-time traffic received by the computer as well as the theoretically maximum value (permanently measured and depending of the type of network connection)

Real-time traffic sent by the computer as well as the theoretically maximum value (permanently measured and depending of the type of network connection)

Number of packets lost or reordered packets received by the client

Real-time CPU usage

Real-time Memory usage

Real-time Disk usage

Because the client is constantly aware of the system and network parameters associated with the machine, it is possible to generate alarms and/or take automatic actions to resolve the problem. For example we can inform the user by generating an alarm that the CPU on his/her machine is too high or has too much packet loss (i.e. that may explain why the audio received is not good). We can also take automatic actions such as reducing the number of videos displayed and/or received if we see that we have too much packet loss or too high CPU usage (i.e. that could mean that the local CPU is not powerful enough to handle several video streams or the connection is not good enough to receive many video streams). Generally, many dedicated actions can be performed automatically and transparently of behalf of the user so he/she always gets the best possible quality during his/her collaborative session and independently of system and network environment that are changing at any time.

To the extreme case where client has lost connection to its attached reflector server (the server maybe has gone down or the network to the dedicated server breaks), the client is capable of reconnecting to an available reflector server in a nearly real-time manner. The user will just notice a short interruption of the service of only a few seconds at most.

Figure 11:
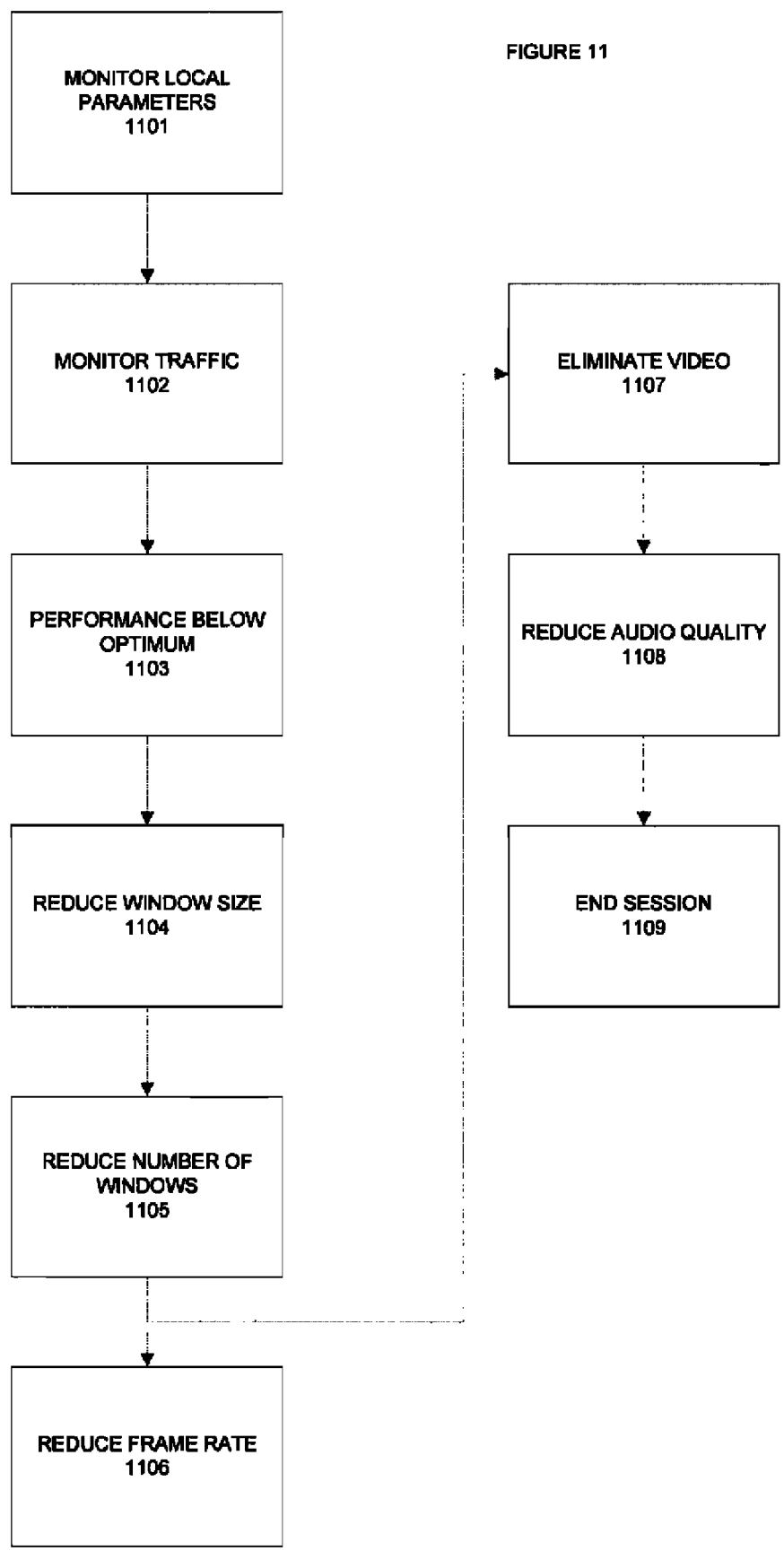
FIG. 11 is a flow diagram illustrating monitoring and management of a client in the system.

FIG. 11 is a flow diagram illustrating the monitoring and management of a client in an embodiment of the system. At step 1101 the local agent monitors local parameters and determines an optimum video presentation based on CPU rate and usage, memory availability and usage, disk usage, and other local parameters. During conferencing, at step 1102, incoming and outgoing traffic is monitored for RTT, packet loss, and other performance parameters. If certain parameters fall below certain thresholds at step 1103, the system goes through a hierarchical series of corrective measures including, but not limited to, reducing video window sizes at step 1104, reducing the number of video windows at step 1105, reducing the video frame rate at step 1106, eliminating video at step 1107, reducing audio quality at step 1108, and ending the session at step 1109. There are other measures that can be taken as well depending on the desires of the user. For example, the system can be assigned preferential access to CPU usage so that if other applications are starving the CPU, the monitor can shut down those applications to free up local computing power for the collaborative session.

IPv6 Compliant

The system main components (client, reflector) are developed in Java so in addition to be multi-platform and running on different Operating Systems, it is also IPv6 compliant. The Java language already included the IPv6 stack which makes any development using this language IPv6 compliant. The system is configured to be backward compatible so that users of IPv4 can function along with users of IPv6.

Multicast Capable

The system includes multicast capability for both the client and the reflector server. By doing so, the system is able to change any non-multicast enabled applications such as an H.323 client (or others) to a multicast enabled application. In order to generalize the use of multicast in the system, the system in one embodiment performs regular monitoring of both communication channels (multicast and unicast connections) and selects dynamically the one that provides the best quality. In this schema, the use of multicast will be transparent from the user and he will always get the best possible connection to perform his/her collaborative meeting.

Video Conference

In one embodiment, the system provides a default video conference mode with selectable options. For example, the user can choose between four different auto-placement modes:

All videos in CIF size (352×288 pixels) automatically arranged on the desktop.

All videos in QCIF size (176×144 pixels) automatically arranged on the desktop.

Only the video of the current speaker, in CIF size.

The video of the current speaker in CIF size, plus all the other videos in QCIF size.

Figure 12:
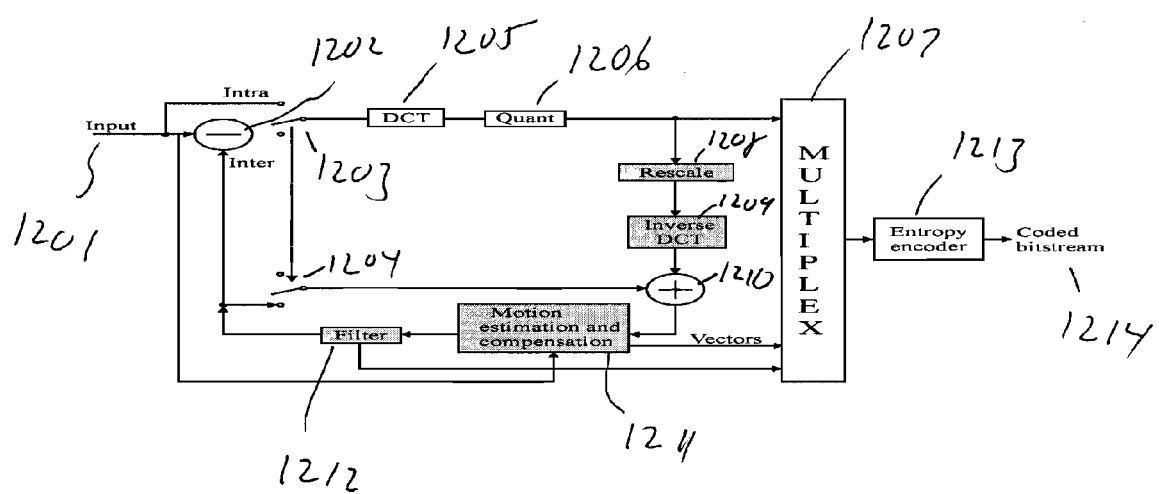
FIG. 12 is a block diagram of a codec for use in one embodiment of the system.

A new H.261 video encoder (illustrated through a block diagram in FIG. 12) is provided in one embodiment. This is fully compliant with the H.261 standard. It takes less bandwidth (higher compression) and provides smoother video. The embodiment provides Inter-frame interpolation as part of the compression algorithm, as indicated in FIG. 12 (contrast with other encoders that use only Intra-frame interpolation.) In Inter-frame mode the difference between two subsequent video frames is computed to remove any temporal redundancy from the video sequence. Then the actual frame is predicted from the decoded reconstructed previous frame, and a residual prediction error (difference) is encoded. Due to the smoothness of the motion that is captured in a sequence of video frames, it is generally very efficient to use Inter-frame interpolation with forward-estimation of the trajectories (expressed through "motion vectors") for small sections (16×16 pixel "macro blocks") of the frame. Then the compression is higher when the previous frame is motion-compensated using the motion vectors. Motion estimation and compensation were added to the new H.261 encoder too. The IPP (Intel Performance Primitives) libraries were used to further improve the performance of VIC, substantially increasing the number of frames per second corresponding to a given level of CPU consumption.

Referring to FIG. 12 input signal 1201 is coupled to difference node 1202. Switch 1203 is used to select between intraframe and interframe operation. Switch 1203 is coupled through DCT 1205 to Quantizer 1206. The output of quantizer 1206 is provided to mux 1207. The output is also coupled in a feedback loop through rescale block 1208 and inverse DCT 1209 to summing node 1210. Switch 1203 is also selectively coupled as an input to summing node 1210. The output of summing node 1210 is coupled through motion estimation and compensation block 1211 and filter 1212 to switch 1204, which selectively couples to difference node 1202 and to switch 1203. Mux 1207 provides output to entropy encoder 1213, which in turns provides a coded bitstream output 1214.

Collaborative Sessions on Mobile Devices

The system includes an application called "PocketVRVS" for use on mobile devices, including those powered by PocketPC operating systems. This software is a full videoconferencing application that allows reception and decoding of audio and video streams received from a VRVS reflector. Moreover it can encode and transmit audio and send CIF sized still images stored in JPEG format in video mode. Due to current limits on CPU performance of mobile devices, the current version of PocketVRVS client doesn't allow sending of live video from Pocket PC cameras. The application supports the H.261 video standard and the G.711 audio standard (An ITU standard for audio compression that requires less CPU power, but more bandwidth than the G.722 standard). The minimum requirements are a Pocket PC with a network (wire/wireless) interface, a 400 MHz CPU and a system such as Windows Mobile 2003 installed.

PocketVRVS works inside any kind of NAT (Network Address Translation) thanks to a specific mechanism that detects the internal and public IP address and automatically matches the UDP ports used by the PocketVRVS application and the reflector. Moreover PocketVRVS continuously sends UDP packets, even if it does not transmit video and/or audio, to ensure that the NAT box maintains the ports and the connection open. To achieve better compatibility with other videoconferencing clients, the application generates RTCP packets that carry basic session information about the user (name, e-mail). First-time users are prompted to enter this information, which can be later changed or modified. The logic of video encoding is adapted to encoding only still images (that means there is no change between subsequent frames). The process is optimized to reach a compromise between frame rate, CPU usage and fast update of video on remote clients.

For handheld videoconferencing it is only practical to display one video at a time because of the limited screen resolution of a handheld computer. This task is carried out by the VRVS reflectors, which can accommodate this new kind of videoconference client, where they send only the video of the current speaker to handheld clients.

A new web-based interface for PocketPC clients (designed for smaller screens) has been created that includes all the controls available for all the clients (meeting scheduler, booking, etc) and also the possibility to connect to an H.323 device. First of all the user has to authenticate himself. Then, he has access to the list of Virtual Rooms booked for a selected date, as well as the list of meetings currently in progress. As on the normal VRVS web site, the user can select a Community and choose the time zone in which the date and time are shown. When the user enters a Virtual Room via a mobile device he must (as usual) type in a password for protected meetings. Once he has come into the Virtual Room he has the choice between two types of videoconference clients. He can start PocketVRVS with 1 click or fill in a form to connect an external H.323 device, triggered by his mobile device. A dedicated auto-installer package that contains the latest PocketVRVS program can be downloaded from the Pocket PC version of the VRVS web site. This package, once downloaded, automatically extracts the content, installs the program and sets up the Windows Mobile Registry. The users connected to a VRVS meeting via mobile devices appear with a special icon in the participant view seen by the meeting participants.

Embodiment of Computer Execution Environment (Hardware)

Figure 10:
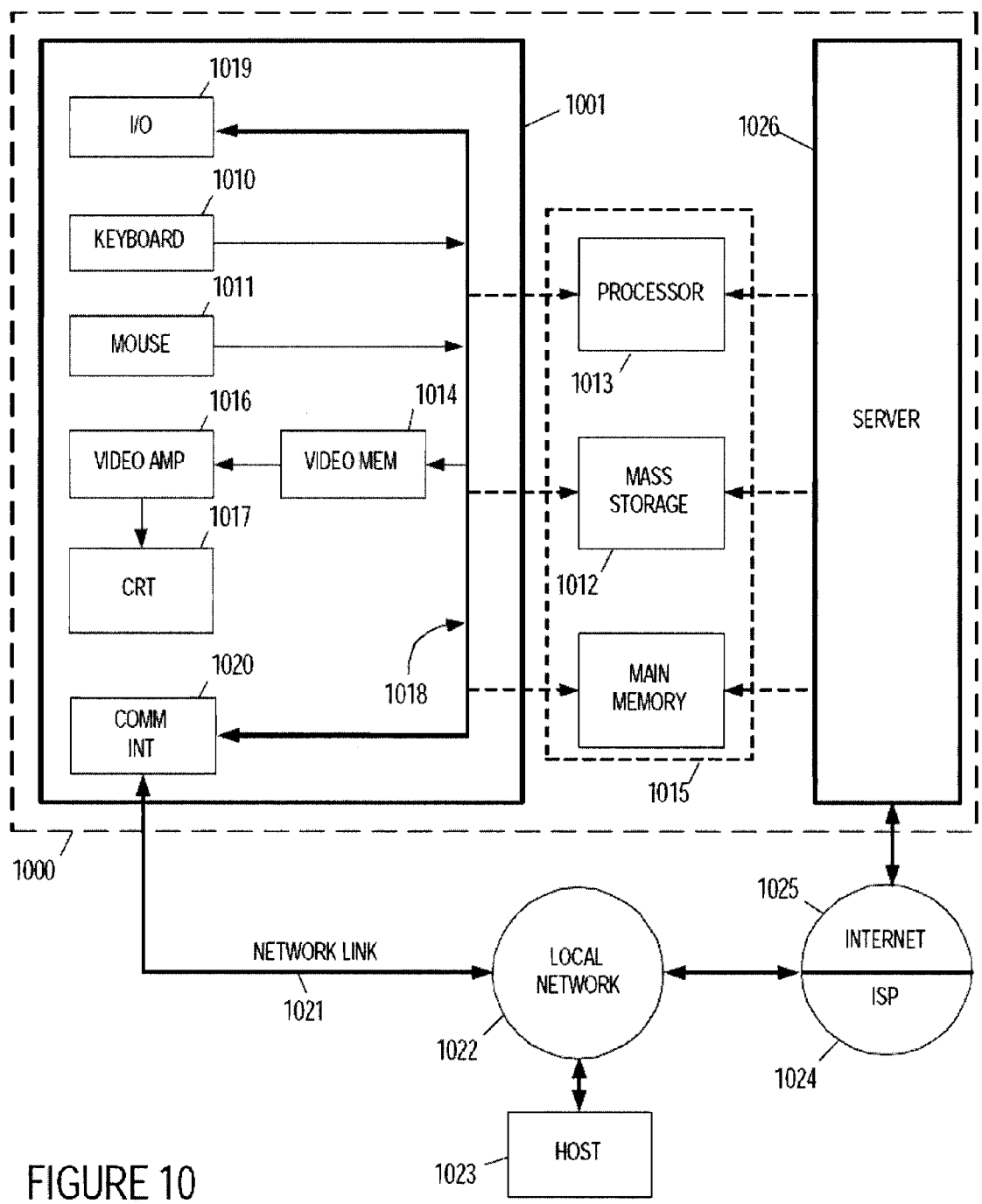
FIG. 10 is an example computer environment of an embodiment of the system.

An embodiment of the invention can be implemented as computer software in the form of computer readable program code executed in a general purpose computing environment such as environment 1000 illustrated in FIG. 10, or in the form of bytecode class files executable within a Java™ run time environment running in such an environment, or in the form of bytecodes running on a processor (or devices enabled to process bytecodes) existing in a distributed environment (e.g., one or more processors on a network). A keyboard 1010 and mouse 1011 are coupled to a system bus 1018. The keyboard and mouse are for introducing user input to the computer system and communicating that user input to central processing unit (CPU) 1013. Other suitable input devices may be used in addition to, or in place of, the mouse 1011 and keyboard 1010. I/O (input/output) unit 1019 coupled to bi-directional system bus 1018 represents such I/O elements as a printer, A/V (audio/video) I/O, etc.

Computer 1001 may include a communication interface 1020 coupled to bus 1018. Communication interface 1020 provides a two-way data communication coupling via a network link 1021 to a local network 1022. For example, if communication interface 1020 is an integrated services digital network (ISDN) card or a modem, communication interface 1020 provides a data communication connection to the corresponding type of telephone line, which comprises part of network link 1021. If communication interface 1020 is a local area network (LAN) card, communication interface 1020 provides a data communication connection via network link 1021 to a compatible LAN. Wireless links are also possible. In any such implementation, communication interface 1020 sends and receives electrical, electromagnetic or optical signals which carry digital data streams representing various types of information.

Network link 1021 typically provides data communication through one or more networks to other data devices. For example, network link 1021 may provide a connection through local network 1022 to local server computer 1023 or to data equipment operated by ISP 1024. ISP 1024 in turn provides data communication services through the worldwide packet data communication network now commonly referred to as the "Internet" 1025. Local network 1022 and Internet 1025 both use electrical, electromagnetic or optical signals which carry digital data streams. The signals through the various networks and the signals on network link 1021 and through communication interface 1020, which carry the digital data to and from computer 1000, are exemplary forms of carrier waves transporting the information.

Processor 1013 may reside wholly on client computer 1001 or wholly on server 1026 or processor 1013 may have its computational power distributed between computer 1001 and server 1026. Server 1026 symbolically is represented in FIG. 10 as one unit, but server 1026 can also be distributed between multiple "tiers". In one embodiment, server 1026 comprises a middle and back tier where application logic executes in the middle tier and persistent data is obtained in the back tier. In the case where processor 1013 resides wholly on server 1026, the results of the computations performed by processor 1013 are transmitted to computer 1001 via Internet 1025, Internet Service Provider (ISP) 1024, local network 1022 and communication interface 1020. In this way, computer 1001 is able to display the results of the computation to a user in the form of output.

Computer 1001 includes a video memory 1014, main memory 1015 and mass storage 1012, all coupled to bi-directional system bus 1018 along with keyboard 1010, mouse 1011 and processor 1013. As with processor 1013, in various computing environments, main memory 1015 and mass storage 1012, can reside wholly on server 1026 or computer 1001, or they may be distributed between the two. Examples of systems where processor 1013, main memory 1015, and mass storage 1012 are distributed between computer 1001 and server 1026 include the thin-client computing architecture developed by Sun Microsystems, Inc., the palm pilot computing device and other personal digital assistants, Internet ready cellular phones and other Internet computing devices, and in platform independent computing environments, such as those which utilize the Java technologies also developed by Sun Microsystems, Inc.

The mass storage 1012 may include both fixed and removable media, such as magnetic, optical or magnetic optical storage systems or any other available mass storage technology. Bus 1018 may contain, for example, thirty-two address lines for addressing video memory 1014 or main memory 1015. The system bus 1018 also includes, for example, a 32-bit data bus for transferring data between and among the components, such as processor 1013, main memory 1015, video memory 1014 and mass storage 1012. Alternatively, multiplex data/address lines may be used instead of separate data and address lines.

In one embodiment of the invention, the processor 1013 is a microprocessor manufactured by Motorola, such as the 680×0 processor or a microprocessor manufactured by Intel, such as the 80×86, or Pentium processor, or a SPARC microprocessor from Sun Microsystems, Inc. However, any other suitable microprocessor or microcomputer may be utilized. Main memory 1015 is comprised of dynamic random access memory (DRAM). Video memory 1014 is a dual-ported video random access memory. One port of the video memory 1014 is coupled to video amplifier 1016. The video amplifier 1016 is used to drive the cathode ray tube (CRT) raster monitor 1017. Video amplifier 1016 is well known in the art and may be implemented by any suitable apparatus. This circuitry converts pixel data stored in video memory 1014 to a raster signal suitable for use by monitor 1017. Monitor 1017 is a type of monitor suitable for displaying graphic images.

Computer 1001 can send messages and receive data, including program code, through the network(s), network link 1021, and communication interface 1020. In the Internet example, remote server computer 1026 might transmit a requested code for an application program through Internet 1025, ISP 1024, local network 1022 and communication interface 1020. The received code may be executed by processor 1013 as it is received, and/or stored in mass storage 1012, or other non-volatile storage for later execution. In this manner, computer 1000 may obtain application code in the form of a carrier wave. Alternatively, remote server computer 1026 may execute applications using processor 1013, and utilize mass storage 1012, and/or video memory 1015. The results of the execution at server 1026 are then transmitted through Internet 1025, ISP 1024, local network 1022 and communication interface 1020. In this example, computer 1001 performs only input and output functions.

Application code may be embodied in any form of computer program product. A computer program product comprises a medium configured to store or transport computer readable code, or in which computer readable code may be embedded. Some examples of computer program products are CD-ROM disks, ROM cards, floppy disks, magnetic tapes, computer hard drives, servers on a network, and carrier waves.

The computer systems described above are for purposes of example only. An embodiment of the invention may be implemented in any type of computer system or programming or processing environment.

Thus a method and apparatus for providing a collaborative system has been described.

What is claimed is:

1. A system for enabling collaborative sessions comprising:
   a network of reflectors, each of the reflectors having a reflector monitoring agent which obtains status information comprising reflector to reflector communication performance and which provides the status information to a register/server;
   a first client which is in communication with only one of the reflectors that is chosen by the first client from a plurality of suggested reflectors identified by the register/server and whose identity was provided to the first client, the first client including a first monitoring agent which obtains first status information concerning the first client and which provides the first status information to the register/server, and wherein said one of the reflectors chosen by the first client is chosen based on a set of criteria comprising at least the proximity of the reflector chosen by the first client to the first client, and the current load on the reflector chosen by the first client, and quality of a network link to the reflector chosen by the first client; and
   a second client which is in communication with only one of the reflectors that is chosen by the second client from a plurality of suggested reflectors identified by the register/server and whose identity was provided to the second client, the second client having a second monitoring agent which obtains second status information concerning the second client and which provides the second status information to the register/server; and wherein
   the register/server is in communication with the network of reflectors and with the first and second client, and wherein the register/server receives status information from the first and second monitoring agents and from each of the reflector monitoring agents, and wherein the register/server controls operations of the clients and reflectors during a collaborative session based on the received status information; and wherein
   the register/server upon request from the first client identifies a plurality of reflectors with which the first client can communicate with and provides the identity of each of the identified reflectors to the first client; and wherein the register/server upon request from the second client identifies a plurality of reflectors with which the second client can communicate with and provides the identity of each of the identified reflectors to the second client.

2. The system of claim 1 wherein the collaborative session comprises a videoconference session.

3. The system of claim 1 wherein the register/server identifies three reflectors with which the first client can communicate with.

4. The system of claim 1 wherein the register/server identifies three reflectors with which the second client can communicate with.

5. The system of claim 1 wherein the first monitoring agent monitors local system performance of the first client and communication performance with said one of the reflectors that was chosen by the first client from the plurality of suggested reflectors identified by the register/server.

6. The system of claim 5 wherein the first monitoring agent takes corrective action automatically when performance falls below desired parameters.

7. The system of claim 6 wherein the first monitoring agent reduces video processing when performance falls below desired parameters.

8. The system of claim 1 wherein the second monitoring agent monitors local system performance of the second client and communication performance with said one of the reflectors that was chosen by the second client from the plurality of suggested reflectors identified by the register/server.

9. The system of claim 8 wherein the second monitoring agent takes corrective action automatically when performance falls below desired parameters.

10. The system of claim 9 wherein the second monitoring agent reduces video processing when performance falls below desired parameters.

11. The system of claim 1, wherein said one of the reflectors chosen by the second client from the plurality of suggested reflectors identified and provided by the register/server was chosen by the second client based on a set of criteria comprising at least the proximity of the reflector chosen by the second client to the second client, and the current load on the reflector chosen by the second client, and quality of a network link to the reflector chosen by the second client.

* * * * *

UNITED STATES PATENT AND TRADEMARK OFFICE
CERTIFICATE OF CORRECTION

PATENT NO.        : 8,316,104 B2
APPLICATION NO.   : 11/559881
DATED             : November 20, 2012
INVENTOR(S)       : Philippe Galvez and Harvey B. Newman It is certified that error appears in the above-identified patent and that said Letters Patent is hereby corrected as shown below:

Column 5,
Line 46, replace "disk 10" with --disk IO--.

Signed and Sealed this
Twenty-second Day of January, 2013

David J. Kappos
*Director of the United States Patent and Trademark Office*